United States Patent
Liu et al.

(10) Patent No.: US 11,627,962 B2
(45) Date of Patent: Apr. 18, 2023

(54) SURGICAL STAPLER MAIN BODY, NAIL BOX, SURGICAL STAPLER AND METHOD OF CONTROLLING SURGICAL STAPLER

(71) Applicant: B. J. ZH. F. PANTHER MEDICAL EQUIPMENT CO., LTD., Beijing (CN)

(72) Inventors: Qing Liu, Beijing (CN); Xiaoqiang Chen, Beijing (CN); Libo Liu, Beijing (CN); Xuelan Yang, Beijing (CN)

(73) Assignee: B. J. ZH. F. PANTHER MEDICAL EQUIPMENT CO., LTD., Beijing (CN)

( * ) Notice: Subject to any disclaimer, the term of this patent is extended or adjusted under 35 U.S.C. 154(b) by 156 days.

(21) Appl. No.: 17/266,175

(22) PCT Filed: Oct. 11, 2019

(86) PCT No.: PCT/CN2019/110655
§ 371 (c)(1),
(2) Date: Feb. 5, 2021

(87) PCT Pub. No.: WO2020/093838
PCT Pub. Date: May 14, 2020

(65) Prior Publication Data
US 2021/0298750 A1 Sep. 30, 2021

(30) Foreign Application Priority Data
Nov. 8, 2018 (CN) .......................... 201811324248.8
Jul. 17, 2019 (CN) .......................... 201910646596.5

(51) Int. Cl.
*A61B 17/072* (2006.01)
*A61B 90/98* (2016.01)
*A61B 17/00* (2006.01)

(52) U.S. Cl.
CPC ............ *A61B 17/072* (2013.01); *A61B 90/98* (2016.02); *A61B 2017/00039* (2013.01);
(Continued)

(58) Field of Classification Search
CPC .............................. A61B 17/072; A61B 90/98
See application file for complete search history.

(56) References Cited

U.S. PATENT DOCUMENTS

2010/0200636 A1* 8/2010 Zemlok .................. A61B 17/10
227/175.1
2015/0122870 A1* 5/2015 Zemlok ............ A61B 17/07207
227/176.1
(Continued)

FOREIGN PATENT DOCUMENTS

CN       103622727 A     3/2014
CN       203458436 U     3/2014
(Continued)

OTHER PUBLICATIONS

Office Action issued in corresponding Canadian patent Application No. 3,109,327, dated May 12, 2022; 5 pgs.
(Continued)

*Primary Examiner* — Nathaniel C Chukwurah
(74) *Attorney, Agent, or Firm* — Hauptman Ham, LLP

(57) ABSTRACT

A surgical stapler body, a cartridge, a surgical stapler and a control method for the surgical stapler. The surgical stapler body includes an identification part capable of identifying information in a storage part that is connected to the cartridge assembly and capable of storing information of the cartridge assembly, the surgical stapler body further comprises a control unit capable of analyzing information stored in the storage part and sending an instruction, a power part capable of providing a power source for the surgical stapler body, and a driving part capable of driving the cartridge
(Continued)

assembly to be closed. On the one hand, it is ensured that the driving part can drive the firing rod to move stably, so as to avoid a large vibration caused by manually operating the firing rod to influence the stitching, and reduce medical risk of human misoperation.

14 Claims, 5 Drawing Sheets

(52) U.S. Cl.
CPC ............ *A61B 2017/00115* (2013.01); *A61B 2017/00398* (2013.01); *A61B 2017/00734* (2013.01); *A61B 2017/07271* (2013.01)

(56) References Cited

U.S. PATENT DOCUMENTS

2016/0100839 A1  4/2016  Marczyk et al.
2016/0256160 A1* 9/2016  Shelton, IV ......... A61B 17/072

FOREIGN PATENT DOCUMENTS

| CN | 103767749 | A | 5/2014 |
|----|-----------|---|--------|
| CN | 104224255 | A | 12/2014 |
| CN | 105411642 | A | 3/2016 |
| CN | 106236175 | A | 12/2016 |
| CN | 108042165 | A | 5/2018 |
| CN | 108209995 | A | 6/2018 |
| CN | 109350157 | A | 2/2019 |
| CN | 110192903 | A | 9/2019 |
| CN | 209678585 | U | 11/2019 |
| EP | 3311761   | A1 | 4/2018 |
| WO | 2019209467 | A1 | 10/2019 |

OTHER PUBLICATIONS

First Office Action issued in corresponding Chinese patent Application No. 201910646596.5, dated Apr. 20, 2020 20 pgs.
Search Report issued in corresponding Chinese patent Application No. 201910646596.5, dated Apr. 10, 2020; 2 pgs.
Office Action issued in corresponding European patent Application No. 19881131.7, dated Aug. 2, 2021; 6 pgs.
International Search Report issued in corresponding International Application No. PCT/CN2019/110655; dated Dec. 30, 2019; State Intellectual Property Office of the P.R. China, Beijing, China, 9 pgs.

* cited by examiner

SURGICAL STAPLER MAIN BODY, NAIL BOX, SURGICAL STAPLER AND METHOD OF CONTROLLING SURGICAL STAPLER

RELATED APPLICATIONS

The present application is a National Phase of International Application Number PCT/CN2019/110655 filed Oct. 11, 2019, and claims priority to Chinese Application Number 201811324248.8 filed Nov. 8, 2018 and Chinese Application Number 201910646596.5 filed Jul. 17, 2019.

TECHNICAL FIELD

The present application relates to the field of medical instruments, and in particular, to a surgical stapler body, a cartridge, a surgical stapler and a control method for the surgical stapler.

BACKGROUND

The working principle of the surgical stapler is the same as that of the stapler, that is, the tissue is stapled by striking implantation of interleaved staples into the tissue. The existing surgical stapler generally controls the firing of the firing rod by means of a mechanical limit, and during operation, the physician selects a cartridge having an appropriate cartridge height and stroke according to the tissue thickness at the site of the cartridge and the length of the tissue that needs to be cut. However, the manual surgical stapler has a problem that the firing force is unstable and causing insufficient stroke of anastomosis. Generally, the surgical stapler body with a fixed working stroke of a surgical stapler matches a cartridge with a specific stroke. That is, the stapler body can only match the cartridge with the specific stroke. In this way, the misoperation due to human artifacts can be avoided. However, when a cartridge with another working stroke for different affected areas in the same patient is needed, the surgical stapler body corresponding to the cartridge with other working strokes can be exchanged. The purchasing cost of the medical instrument is increased, and it is troublesome to maintain the posterior instrument.

SUMMARY

A first object of the present application is to provide a surgical stapler body capable of reducing medical risk and reducing medical instrument use cost.

In order to achieve the above object, the technical solution adopted is that: a surgical stapler body comprises an identification part capable of identifying information in a storage part connectable to a cartridge assembly for storing information of the cartridge assembly, the surgical stapler body further comprises a control unit capable of analyzing the information stored in the storage part and sending an instruction, a power part capable of providing a power source for the surgical stapler body and a driving part capable of driving the cartridge assembly to be closed.

Compared with the prior art, the technical effect of the present application is that: the cartridge component the information of the cartridge assembly is received by the identification part. The control unit analyzes the information stored in the storage part. After the driving part receives the control instruction sent by the control unit, the driving part drives the cartridge assembly to be closed. On the one hand, it is ensured that the driving part can drive the cartridge assembly to stably clamp the tissue to be treated and fire staples, to avoid the large vibration caused by the movement of the firing rod 31 in manual operation to affect the stitching, and reduce medical risk of human misoperation; on the other hand, the surgical stapler body of the present application can adapt a plurality of types of staples, so that it is unnecessary to purchase a plurality of types of surgical stapler body to cooperate with the corresponding cartridge, thereby greatly reducing the purchase cost of the medical instrument and the maintenance cost of the additionally purchased surgical stapler body.

A second object of the present application is to provide a cartridge that reduces medical risk and is convenient to use.

In order to achieve the above object, the technical solution adopted is that: a cartridge comprises a storage part connected to the cartridge assembly, wherein the information stored in the storage part comprises preset stroke data of the cartridge.

Compared with the prior art, the technical effects of the present application are that: the storage part of the cartridge is placed at the identification part of the surgical stapler body, so that the data stored in the storage part of the cartridge can be received by the identification portion, and the control unit of the surgical stapler converts the received preset stroke data into a control instruction and sends the control instruction to the driving part, and the driving part drives the cartridge to operate according to the control instruction. The cartridge and the surgical stapler body are used in cooperation, and on the one hand, the cartridge is prevented from affecting the stapling by manually operating the firing rod, and the medical risk of manually operating is reduced. On the other hand, when a cartridge of another model is used, the control unit receives preset stroke data of the cartridge, the replacement of the cartridge is convenient, and the operation is simple and convenient.

A third object of the present application is to provide a surgical stapler comprising the surgical stapler body and the above cartridge.

A fourth object of the present application is to provide a control method for a surgical stapler.

In order to achieve the above object, the technical solution adopts a control method for a surgical stapler, which comprises:

the identification part reads the preset stroke data of the cartridge;

the control unit calculates the number of rotating turns of the rotating shaft of the motor of the driving part according to the preset stroke data of the cartridge;

the control unit receives a user instruction, and the control unit sends a control instruction to control the operation of the motor.

Compared with the prior art, the technical effects of the present application are as follows: by means of the described control method, on the one hand, the driving part can drive the firing rod to move stably, so as to avoid the large vibration influence stitching caused by manual operation, and reduce the medical risk of human misoperation. On the other hand, a plurality of types of cartridges can be adapted, so that it is unnecessary to purchase a plurality of types of cartridge bodies to cooperate with corresponding cartridges, thereby the purchase cost of the medical instrument and the maintenance cost of the additionally purchased cartridge bodies are reduced.

Figure 1:
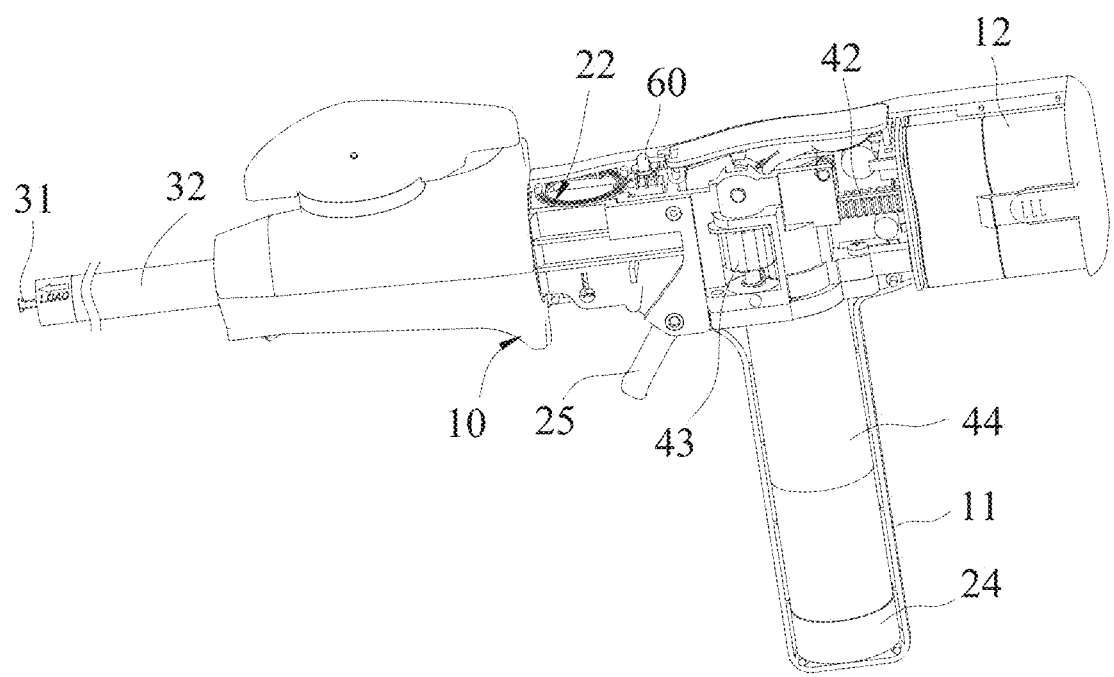
FIG. 1 is a diagram of the structure of the surgical stapler body removing part of the housing of the present application.

In the reference numerals, 10—housing, 11—handle housing, 12—battery; 21—firing confirmation switch, 22—identification part, 23—sensing part, 24—Hall encoder, 25—firing switch; 31—firing rod, 32—conduit; 41—mounting pipe, 42—transmission, 421—protrusion, 43—gear, 44—motor; 50—cartridge, 51—cartridge assembly, 52—storage part, 53—cartridge base, 54—staple cartridge, 55—push rod, 56—push staple member; 60—indicator lamp.

DETAILED DESCRIPTION

Hereinafter, the embodiments of the present application will be described with reference to the accompanying drawings.

Herein, "upper", "lower", "front", "rear", "left", "right", and the like are merely used to represent relative positional relationships between relevant parts, and not to limit the absolute positions of these relevant parts.

Herein, "first", "second", and the like are used for differentiating each other only, and do not represent the degree and order of importance, as well as the prerequisite of mutual presence, and the like.

Herein, "equal", "identical", "identical", and the like are not strictly mathematical and/or geometrical limitations, but also contain errors that can be understood by those skilled in the art and allowed by manufacture or use and the like.

Unless otherwise specified, the numerical ranges herein include not only the entire range between its two endpoints, but also a number of sub-ranges included therein.

Figure 2:
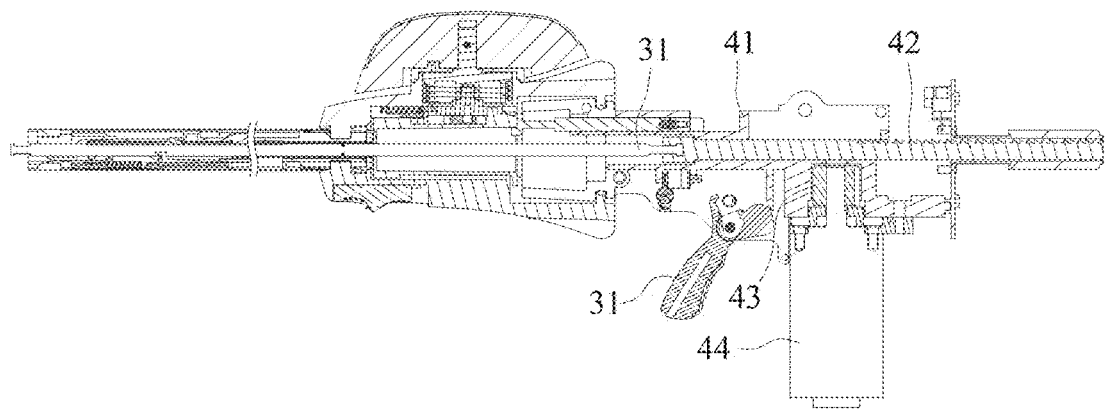
FIG. 2 is a sectional view of the surgical stapler body of the present application.
Figure 3:
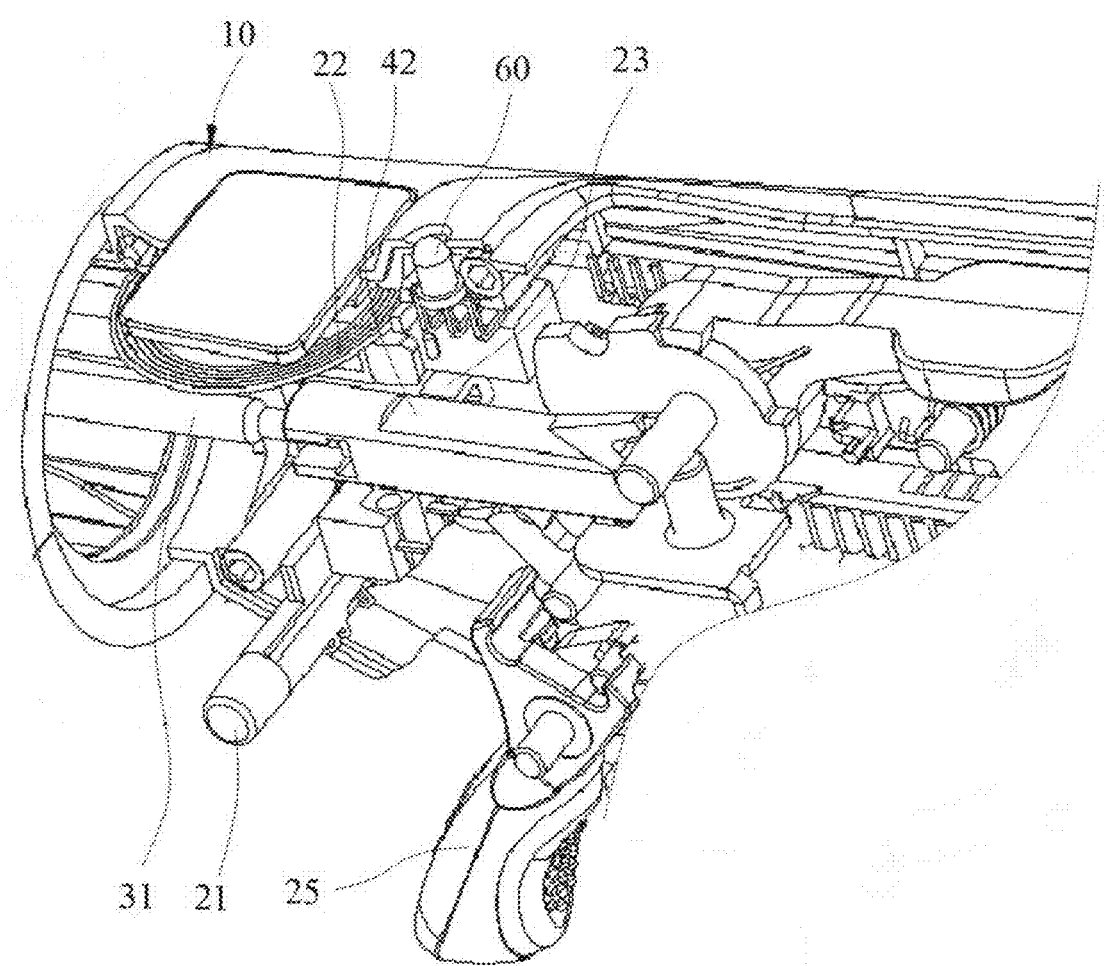
FIG. 3 is a partial diagram of the surgical stapler body of the present application.

Referring to FIGS. 1 to 3, a surgical stapler body is provided. The surgical stapler body comprises an identification part 22 capable of identifying information in a storage part 52 connected to a cartridge assembly 51 for storing the information of the cartridge assembly, the surgical stapler body further includes a control unit that can analyze the information stored in the storage part 52 and send an instruction, a power part capable of providing a power source for the surgical stapler body, and a driving part capable of driving the cartridge assembly 51 to be closed.

The identification part 22 receives the information of the cartridge assembly 51. The control unit analyzes the information stored in the storage part 52. The driving part drives the cartridge assembly 51 to be closed after receiving a control instruction sent by the control unit. On the one hand, it is ensured that the driving part can drive the cartridge assembly 51 to stably clamp the tissue to be treated and then fire staples, to avoid the large vibration caused by manual operation to affect the stitching, and reduce medical risk of human misoperation; on the other hand, the surgical stapler body of the present application can adapt a plurality of types of cartridges, so that it is unnecessary to purchase a plurality of types of surgical stapler body to cooperate with the corresponding cartridge, thereby greatly reducing the purchase cost of the medical instrument and the maintenance cost of the additionally purchased surgical stapler body.

The surgical stapler body further comprises a housing 10, and a driving part is arranged in the housing cavity of the housing 10. The driving part is connected to one end of the firing rod 31, and the other end of the firing rod 31 is connected to the cartridge 50. The rod body of the firing rod 31 is located in a conduit 32. The control unit receives the preset stroke data of the storage part 52 read by the identification part 22 to convert the preset stroke data into a control instruction and send the control instruction to the driving part. The driving part receives a control instruction to drive the firing rod 31 to move in the guiding direction of the conduit 32.

In the above embodiment of the present application, a cartridge 50 of a model corresponds to a specific working stroke. The working stroke includes a cartridge closing stroke and a cartridge striking stroke. The control unit receives the preset stroke data of the cartridge 50 to convert the preset stroke data into a control instruction and send the control instruction to the driving part. The driving part drives the firing rod 31 to move according to the control instruction. On the one hand, it is ensured that the firing rod 31 can be moved precisely to a required distance, the driving part can drive the firing rod 31 to stably move, to avoid the large vibration caused by the movement of the firing rod 31 in manual operation to affect the stitching, and reduce medical risk of human misoperation; on the other hand, when replacing to the cartridge 50 of another model, the control unit receives the preset stroke data of the cartridge 50, and convert the preset stroke data of the cartridge 50 of other model into corresponding control instructions and send the control instructions to the driving part, to complete the firing of the cartridge 50 of other model. Therefore, the surgical stapler of the present application can be adapted to a plurality of types of cartridges, so that it is not necessary to purchase surgical stapler bodies of various models to cooperate with corresponding cartridges. The purchase cost of the medical device and the maintenance cost of the additional purchased surgical stapler body are greatly reduced.

The identification part 22 is arranged on the circuit board, the identification part 22 is located on the outer side or the inner side of the housing 10, and the identification part 22 reads the preset stroke data of the cartridge 50, which includes the cartridge closing stroke data and the staple firing stroke data.

The identification part 22 may be an RFD (Radio Frequency Identification) reader, and the RFID reader can read electronic tag data, that is, the RFID reader is configured to receive the preset stroke data of the cartridge 50. The identification part 22 includes an identification coil, and the identification part 22 is provided on an outer side or an inner side of the housing 10. Depending on the actual conditions of use, the identification part 22 is provided at an appropriate position of the surgical stapler, for example, the identification portion 22 is provided at a rear end portion or a top portion or a side portion of the surgical stapler.

The driving part comprises a mounting pipe 41, the mounting pipe 41 is connected to an inner wall of the housing 10. A transmission 42 is arranged in the mounting pipe 41, and the mounting pipe 41 defines the movement of the transmission 42 along a guiding direction of the firing rod 31, one end of the transmission 42 is connected to the firing rod 31. The power unit of the driving part is cooperatively transmitted with the transmission 42.

The mounting pipe 41 defines the movement of the transmission 42 along the guiding direction of the firing rod 31 to ensure stable operation of the transmission 42, and ensure the movement of the firing rod 31, so as to enable stable operation of the cartridge closure process of the cartridge 50 and the firing process of the staple in the cartridge 50.

Figure 4:
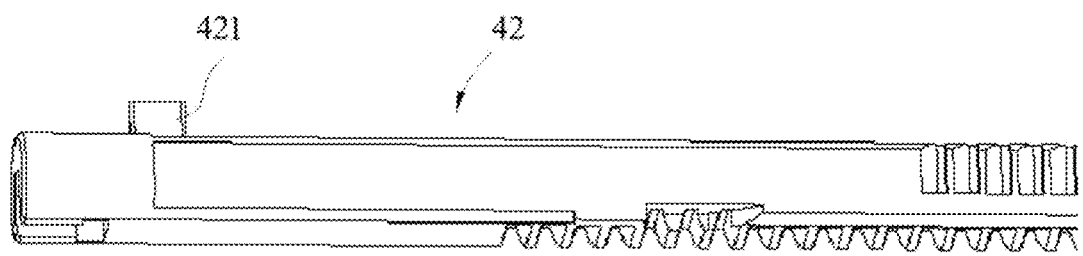
FIG. 4 is a diagram of the structure of the transmission of the surgical stapler body of the present application.

Referring to FIG. 4, after the cartridge 50 completes the firing operation, the firing rod 31 needs to be reset for the next use. In the present application, a protrusion 421 is provided on the transmission 42. The control unit further comprises a sensing part 23 arranged in the housing cavity of the housing 10. The sensing region of the sensing part 23 is located in the movement path of the protrusion 421 on the transmission member 42. The power unit stops operation until the power unit drives the protrusions 421 on the transmission 42 to reset and move into the sensing area of the sensing part 23.

By providing the protrusion 421 on the transmission 42, the sensing area of the sensing part 23 is provided in the movement path of the protrusion 421 on the transmission 42. The sensing part 23 may be a zero-position sensing element, so that the power unit drives the protrusion 421 on the transmission part 42 to be reset and moved into the sensing area of the sensing part 23. The reset of the firing rod 31 is completed by the cooperation between the protrusion 421 and the sensing part 23. The protrusion 421 on the transmission 42 has a simple structure and can be easily manufactured, and the manufacturing cost of the surgical stapler is saved.

It should be noted that, as long as the structure that enables the transmission 42 to drive the firing rod 31 to move within the conduit 32 is allowed, the specific structure of the preferred driving part is provided below in the present application.

The transmission 42 is a rack, and the mounting pipe 41 is provided with a rack, and the mounting pipe 41 defines the movement of the rack along the guiding direction of the firing rod 31, one end of the rack is connected to the firing rod 31. The power unit is an electric motor 44, the rotation shaft of the electric motor 44 is coaxially connected to the gear 43, and the gear 43 is engaged with the rack for transmission.

The mounting pipe 41 is of a square tubular shape, the front section of the rack may be arranged in a square shape, the front section of the rack is cooperated with the mounting pipe 41 to define the movement of the rack along the guiding direction of the firing rod 31, and the rear part of the rack may be machined into a tooth shape to mesh with the gear 43 for transmission. According to the actual arrangement position of the rack, at least one intermediate gear may be provided to be engaged with the rack and the gear 43 to achieve transmission.

The control unit further includes a Hall encoder 24 disposed on the power unit to monitor the operation of the power unit.

The Hall encoder 24 monitors the operation state of the motor 44, and determines the number of turns or angle of operation of the motor 44 by pulse information fed back by the Hall encoder 24.

Figure 5:
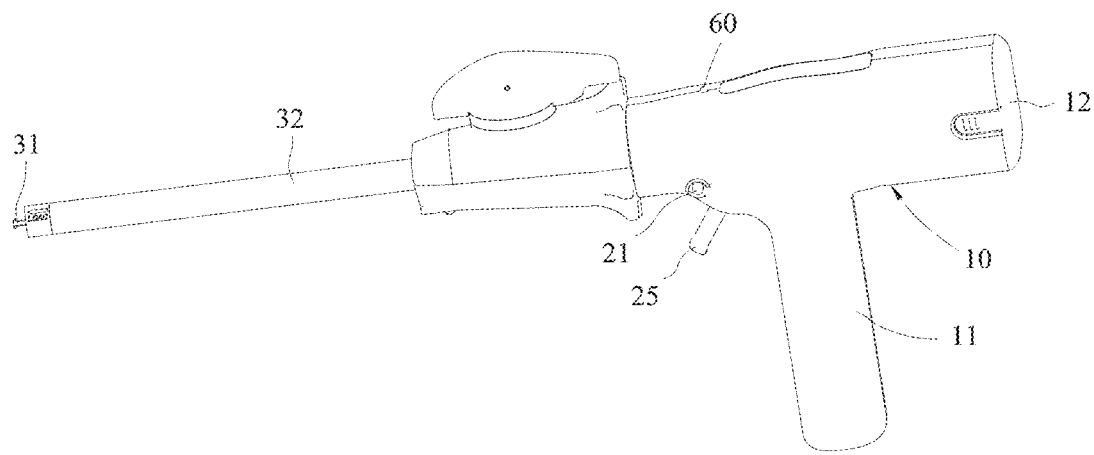
FIG. 5 is a diagram of the overall structure of the surgical stapler body of the present application.

Referring to FIG. 5, the housing 10 is in a tubular shape as a whole, the housing 10 is provided with a handle housing 11 extending radially along the housing 10, the motor 44 is located in the housing cavity of the handle housing 11 of the housing 10, a power part is provided in the housing cavity of a rear end portion of the housing 10, the power part comprises a battery 12, and the battery 12 is electrically connected to the motor 44. By arranging the handle housing 11, on the one hand, an operator can conveniently hold the handle housing 11, on the other hand, the motor 44 is arranged in the housing cavity formed by the handle housing 11, and the space of the housing cavity is effectively used to reduce the volume of the surgical stapler. The battery 12 may be detachably connected to the rear end of the housing 10, and the battery 12 supplies power to the control unit and the motor 44.

Figure 6:
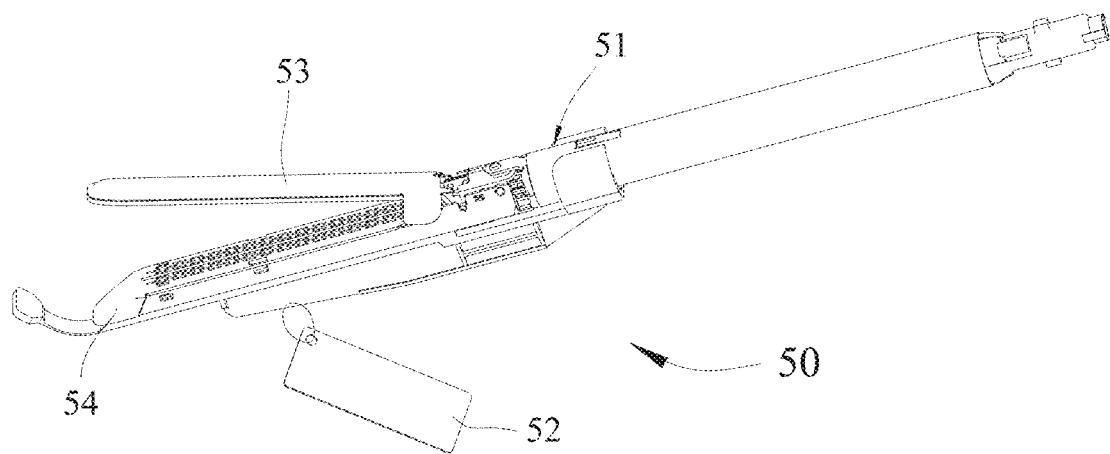
FIG. 6 is a schematic perspective view of a cartridge of the present application.

Referring to FIG. 6, the present application further discloses a cartridge, comprising a storage part 52 connected to the cartridge assembly 51, and the information stored in the storage part 52 comprises preset stroke data of the cartridge 50.

The storage part 52 of the cartridge 50 is placed at the identification portion 22 of the surgical stapler body by the storage part 52 provided on the cartridge assembly 51 of the cartridge 50, so that the data stored in the storage part 52 of the cartridge 50 can be received by the identification part 22, and the control unit of the surgical stapler body converts the received preset stroke data into a control instruction and sends the control instruction to the driving part, and the driving part drives the cartridge assembly 51 to work according to the control instruction.

When using other type of the cartridge assembly 51 of the cartridge 50, the cartridge assembly 51 is provided with a corresponding storage part 52, the storage part 52 stores preset stroke data of the other type of the cartridge assembly 51. The control unit receives the preset stroke data of the cartridge 50. The preset stroke data of the other type of cartridge 50 are converted into corresponding control instructions, and the control instructions are sent to the driving part, so as to complete the firing operation of the other type of the cartridge 50. Since the cartridge 50 cooperates with the surgical stapler body, on the one hand, it is ensured that the firing rod 31 can be moved precisely to a required distance, and the driving part can drive the firing rod 31 to stably move, to avoid the large vibration caused by the movement of the firing rod 31 in manual operation to affect the stitching, and reduce medical risk of human misoperation; on the other hand, when replacing to the other type of the cartridge 50, the control unit receives the preset stroke data of the cartridge 50, the preset stroke data of the type of the cartridge 50 is converted into corresponding control instructions, and the control instructions are sent to the driving part, so as to complete the firing operation of the other type of the cartridge 50. Therefore, the surgical stapler of the present application can be adapted to a plurality of types of cartridges, so that it is not necessary to purchase surgical stapler bodies of various models to cooperate with corresponding cartridges. The purchase cost of the medical device and the maintenance cost of the additional purchased surgical stapler body are greatly reduced.

Preferably, the storage part 52 and the cartridge assembly 51 form a detachable connection, and the storage part 52 is an electronic tag attached to the outer circumferential surface of the cartridge assembly 51 or hanged to the cartridge assembly 51.

If the storage part 52 is fixed to the cartridge assembly 51, the cartridge 50 is hold to place the electronic tag at the identification part of the surgical stapler, and if the storage part 52 is an electronic tag attached to the outer circumferential surface of the cartridge assembly 51 or an electronic tag hanged to the cartridge assembly 51, the cartridge 50 is mounted to the surgical stapler, and then the electronic tag is removed and placed at the identification part of the surgical stapler body.

In addition, an electronic tag is connected to the cartridge protective sleeve, and the control unit pre-enters the cartridge parameter information corresponding to different types of cartridges, and can be coupled to the surgical stapler via the data line of the scanner. In use, the scanner firstly scans the cartridge model with the optical character identification technology to obtain stroke data corresponding to the nail cartridge 50.

Preferably, the storage part 52 is an electronic tag, and the electronic tag is one of a card with a magnetic stripe, an inductive electronic wafer and an integrated circuit card, as long as the electronic tag can store data.

Figure 7:
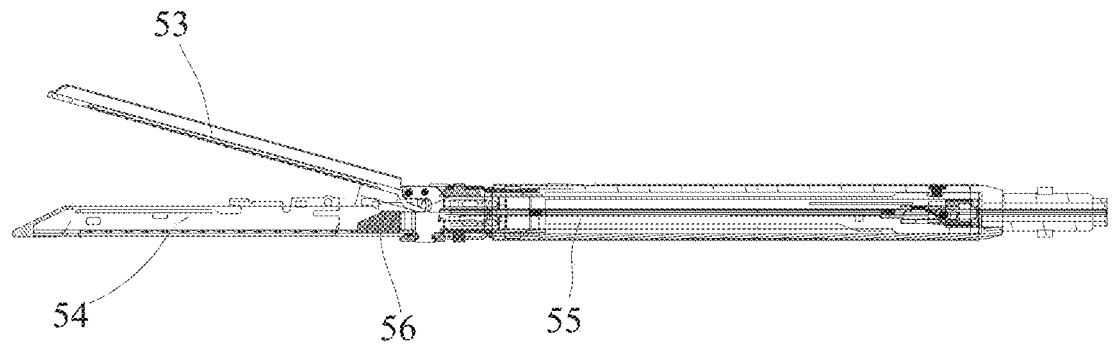
FIG. 7 is a sectional view of the cartridge assembly of the present application.

Referring to FIG. 7, the main structure of the cartridge assembly 51 will be described below.

The cartridge assembly 51 comprises a cartridge base 53, the cartridge base 53 is hinged to the housing of the cartridge assembly 51, the cartridge base 53 is correspondingly arranged with a staple cartridge 54, and the push rod 55 drives the suspended end of the cartridge base 53 to rotate and cooperate with the staple cartridge 54 to clamp tissue to be treated. The push rod 55 drives the push staple member 56 to move to fire the staple in the staple cartridge 54.

Figure 8:
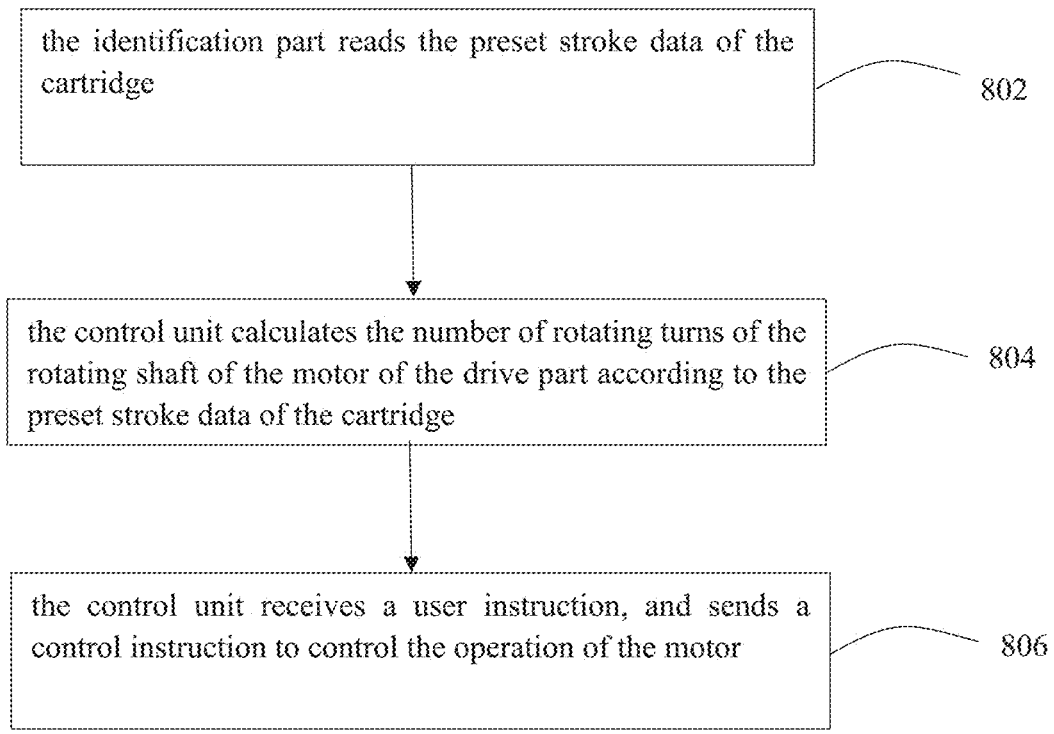
FIG. 8 is a flowchart of a method for controlling the surgical stapler according to an embodiment of the present application.

It should be noted that the cartridge assembly 51 may adopt an existing disposable cartridge, and the cartridge assembly 51 is not limited herein in the present application. Referring to FIG. 8, an embodiment of the present application discloses a control method for a surgical stapler, wherein the surgical stapler comprises a surgical stapler body and a cartridge 50, and the control method comprises:

Step 802: the identification part 22 reads the preset stroke data of the cartridge 50. The identification part 22 reads data including, but not limited to, preset stroke data and validity period data of the cartridge 50, and for the expired data of the cartridge 50, the control unit may send a sound or display warning, that is, the cartridge 50 cannot be used, and the control unit identifies that the success of the cartridge 50 will send a prompt different from the expiry warning, that is, the cartridge 50 can be used normally.

Step 804: the control unit calculates the number of rotating turns of the rotating shaft of the motor 44 of the drive part according to the preset stroke data of the cartridge 50.

The control unit calculates by the formula (1).

$$n = L/(\pi d/i_1/i_2) \quad (1)$$

wherein, n is the number of rotational stitches of the rotating shaft of the motor; L is a preset stroke of the cartridge; d is the diameter of the final gear indexing circle; $i_1$ is the transmission ratio of the driving part; $i_2$ is the motor deceleration ratio.

Step 806: the control unit receives a user instruction, and sends a control instruction to control the operation of the motor 44.

In the above embodiment, the control unit receives the preset stroke data of the cartridge 50 to convert into a control instruction and sends the control instruction to the driving part. The driving part drives the firing rod 31 to move according to the control instruction. According to the control method of the surgical stapler of the present application, on the one hand, It is ensured that the firing rod 31 can be moved precisely to a desired distance, he and the driving part can drive the firing rod 31 to stably move, to avoid the large vibration caused by the movement of the firing rod 31 in manual operation to affect the stitching, and reduce medical risk of human misoperation; on the other hand, a plurality of types of cartridges can be adapted, so that the stapler main body of a plurality of models does not need to be purchased to cooperate with the corresponding cartridge, thereby greatly reducing the purchase cost of the medical instrument and the maintenance cost of the additionally purchased stapler main body.

An embodiment of the present application discloses a surgical stapler comprising the surgical stapler body and the cartridge 50 as described above.

Figure 9:
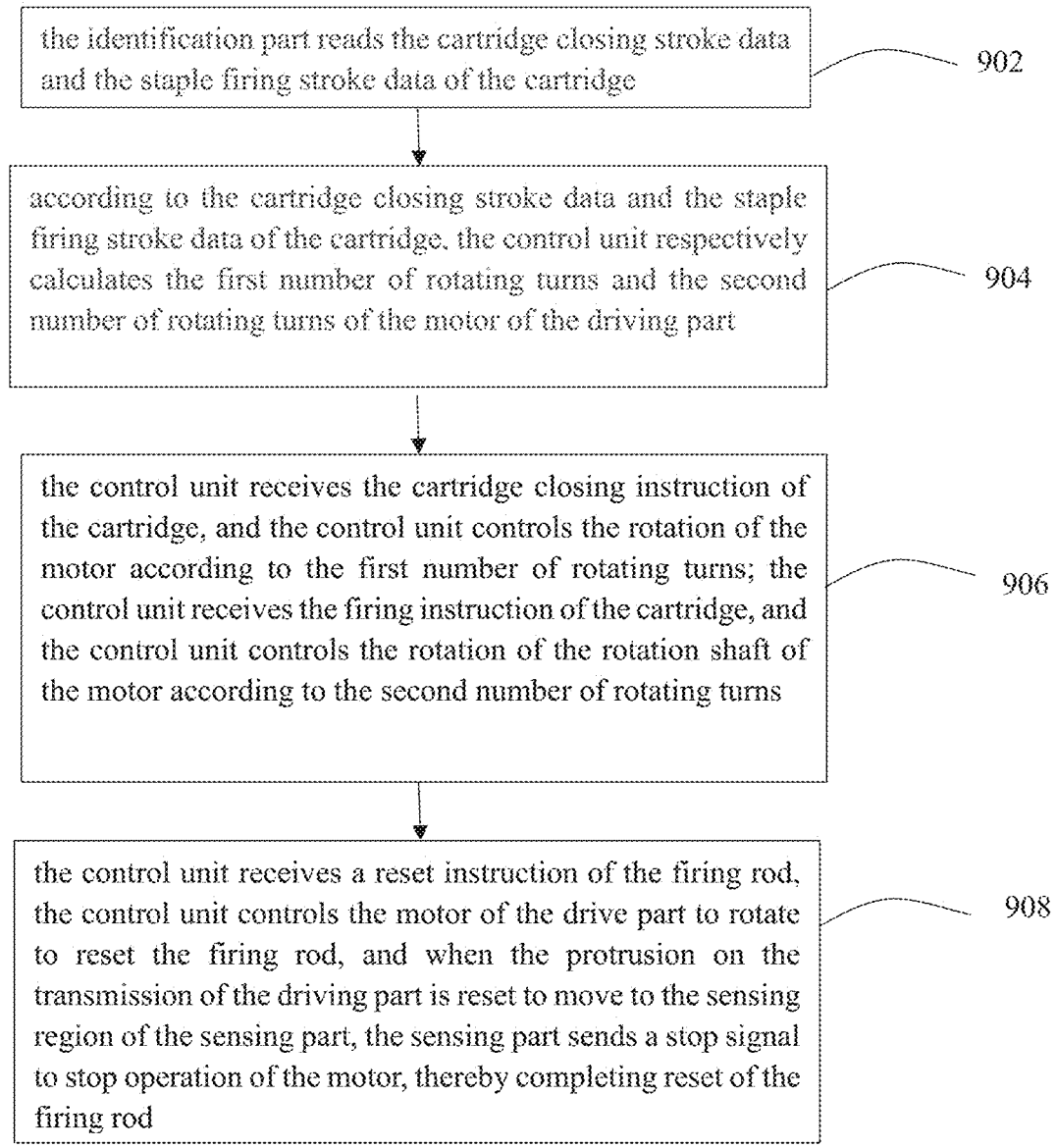
FIG. 9 is a flowchart of a method for controlling the surgical stapler according to another embodiment of the present application.

Referring to FIG. 9, another embodiment of the present application discloses a control method for a surgical stapler, comprising:

Step 902: the identification part 22 reads the cartridge closing stroke data and the staple firing stroke data of the cartridge 50.

Step 904: according to the cartridge closing stroke data and the staple firing stroke data of the cartridge 50, the control unit respectively calculates the first number of rotating turns and the second number of rotating turns of the motor 44 of the driving part.

It should be noted that, the total number of rotating turns of the rotating shaft of the motor 44 is calculated according to the cartridge closing stroke data and the staple firing stroke data of the cartridge 50, in other words, the total number of rotating turns of the rotating shaft of the motor 44 is divided into the first number of rotating turns and the second number of rotating turns, and the first number of rotating turns and the second number of rotating turns respectively correspond to the cartridge closing stroke data and the staple firing stroke data.

Step 906: the control unit receives the cartridge closing instruction of the cartridge 50, and the control unit controls the rotation of the motor 44 according to the first number of rotating turns;

The control unit receives the firing instruction of the cartridge 50, and the control unit controls the rotation of the rotation shaft of the motor 44 according to the second number of rotating turns.

Step 908: the control unit receives a reset instruction of the firing rod 31, the control unit controls the motor 44 of the drive part to rotate to reset the firing rod 31, and when the protrusion 421 on the transmission 42 of the driving part is reset to move to the sensing region of the sensing part 23, the sensing part 23 sends a stop signal to stop operation of the motor 44, thereby completing reset of the firing rod 31.

In this way, the protrusion 421 on the transmission part 42 of the driving part is reset and moved to the sensing area of the sensing part 23, and the protrusion 421 is cooperated with the sensing part 23, so that the reset of the striking lever 31 is completed accurately, and the firing rod 31 is reset without manual operation, which brings convenience to the use of the surgical stapler.

In the above embodiment, the control unit receives the preset stroke data of the cartridge 50. The control unit calculates the first number of rotating turns and the second number of rotating turns of the motor 44 of the driving part. The driving part drives the firing rod 31 to accurately move according to the control instruction. It is ensured that the firing rod 31 can move accurately in the cartridge closing stroke and the cartridge firing stroke, the medical risk of human operation is reduced and the stitching quality of the tissue to be treated is improved.

The actual operation process of the surgical stapler of the present application will be described in further detail below.

The battery 12 is loaded into the surgical stapler body, and the indicator lamp 60 on the surgical stapler after the battery 12 is docked successfully indicates that power is successfully energized. Then, the electronic tag on the cartridge assembly 51 is removed. The surgical stapler body is identified and read at the reading area of the identification part 22. The identification part 22 successfully identifies the preset stroke data stored in the electronic tag. The operator grips the trigger to trigger the firing switch 25. The firing switch 25 is normally closed as a continuous signal, otherwise is an intermittent signal. The forward operation of the rotating shaft of the motor 44 drives the rack and the firing rod 31 to be displaced distally. When the cartridge base 53 and the staple cartridge 54 are closed in position to clamp the tissue to be treated, the motor 44 stops running. When the staple cartridge 54 is closed, the operator stops triggering the firing switch 25 and the motor 121 stops running.

After the staple cartridge 54 is closed, the operator presses the trigger confirmation button to trigger the firing confirmation switch 21, and then the firing switch 25 is triggered, and the rotating shaft of the motor 44 continues to rotate forward, so that the rack and the firing rod 31 are displaced distally, and after the firing of the cartridge is completed. During the closing process of the above staple cartridge 54, the operator stops triggering the firing switch 25 and the motor 121 stops running.

When the control unit determines that the cartridge triggering is completed, the operator stops triggering the firing switch 25, and the protrusion 421 on the rotating shaft of the motor 44 reverses the rack of the rotating shaft to move to the sensing area of the sensing part 23, and the sensing part 23 sends a stop signal to the motor 44 to stop the motor 44 and reset the firing rod 31.

It should be noted that the operator stops triggering the firing switch 25 at any position other than the cartridge closing end position and the cartridge firing end position, so that the motor 44 stops running. At any position other than the cartridge firing end position, the operator stops triggering the firing switch 25, and after the motor 44 stops running, the trigger is pushed upward to trigger the return switch, and the rotation shaft of the motor 44 is reversed to reset the trigger lever 31.

The preferred embodiments of the present application are described in detail above with reference to the accompanying drawings, but the present application is not limited to the above embodiments, and various changes may be made within the knowledge provided by those skilled in the art without departing from the concept of the present application.

The invention claimed is:

1. A surgical stapler body, comprising:
   an identification part configured to
      (i) identify information in a storage part connected to a cartridge assembly and
      (ii) store information of the cartridge assembly;
   a control unit configured to analyze information stored in the storage part and send an instructions;
   a power part configured to provide a power source for the surgical stapler body;
   a driving part configured to drive the cartridge assembly to be closed; and
   a cartridge comprising a storage part connected to a cartridge assembly, and information able to be stored in the storage part comprises preset stroke data of the cartridge, wherein
   the storage part and the cartridge assembly are detachably connected, and the storage part is an electronic tag attached to an outer circumferential surface of the cartridge assembly or an electronic tag hanged to the cartridge assembly,
   the storage part and the cartridge assembly are detachably connected, and
   the storage part is an electronic tag attached to an outer circumferential surface of the cartridge assembly or an electronic tag hanged to the cartridge assembly.

2. The surgical stapler body according to claim 1, further comprising:
   a housing;
   a driving part in a housing cavity of the housing;
   a firing rod, wherein the driving part is connected to one end of the firing rod, and the other end of the firing rod is connected to the cartridge;
   a rod body of the firing rod in a conduit, wherein
   the control unit is configured to
      (i) receive preset stroke data of the storage part read by the identification part,
      (ii) convert the preset stroke data into a control instruction, and
      (iii) send the preset stroke data to the driving part, and
   the driving part is configured to receive the control instruction to drive the firing rod to move in a guiding direction of the conduit.

3. The surgical stapler body according to claim 2, wherein the identification part is on a circuit board, the identification part is on an outer side or an inner side of the housing, and the identification part is configured to read the preset stroke data of the cartridge comprising cartridge-closing stroke data and staple-firing stroke data.

4. The surgical stapler body according to claim 3, wherein the driving part comprises
   a mounting pipe, the mounting pipe is connected to an inner wall of the housing;
   a transmission in the mounting pipe, wherein the mounting pipe defines the movement of the transmission along the guiding direction of the firing rod, one end of the transmission is connected to the firing rod; and
   a power unit configured to cooperate with the transmission.

5. The surgical stapler body according to claim 4, wherein the transmission comprises a protrusion,
   the control unit further comprises a sensing part in the housing cavity of the housing, a sensing region of the sensing part is in a movement path of the protrusion of the transmission, the power unit is configured to drive the protrusion of the transmission to return back to the sensing area of the sensing part, and the power unit is configured to stop.

6. The surgical stapler body according to claim 4, wherein the transmission is a rack, the rack is in the mounting pipe, and the mounting pipe is configured to limit the rack to move along the guiding direction of the firing rod, one end of the rack is connected to the firing rod, the power unit is a motor, and a rotating shaft of the motor is coaxially connected to a gear and the gear is engaged with the rack for the transmission.

7. The surgical stapler body according to claim 6, wherein the housing is tubular, the housing comprises a handle housing extending radially along the housing, the motor is in a housing cavity of the handle housing, a power part is in the housing cavity of a rear end portion of the housing, the power part comprises a battery, and the battery is configured to be electrically connected to the motor.

8. A control method of the surgical stapler of claim 6, comprising:

reading, by the identification part, of the preset stroke data of the cartridge;

calculating, by the control unit, of a number of rotating turns of the rotating shaft of the motor of the driving part according to the preset stroke data of the cartridge;

receiving, by the control unit, of a user instruction, and sending, by the control unit, of a control instruction to control an operation of the motor.

9. The control method of the surgical stapler according to claim 8, wherein the reading, by the identification part, of the preset stroke data of the cartridge, comprises reading of the cartridge-closing stroke data and the staple-firing stroke data of the cartridge;

the calculating, by the control unit, of the number of rotating turns of the rotating shaft of the motor of the driving part according to the preset stroke data of the cartridge, comprises calculating of the cartridge-closing stroke data and the staple-firing stroke data of the cartridge, and a first number of rotating turns and a second number of rotating turns of the motor of the driving part;

the receiving, by the control unit, of the user instruction comprises receiving of cartridge-closing instruction of the cartridge, and a firing instruction of the cartridge, and the sending, by the control unit, of the control instruction to control the operation of the motor comprises controlling of rotation of the rotating shaft of the motor according to the first number of rotating turns, and the rotation of the rotating shaft of the motor according to the second number of rotating turns.

10. The control method of a surgical stapler according to claim 8, wherein the receiving, by the control unit, of the user instruction comprises receiving of a reset instruction of the firing rod, and the sending, by the control unit, of the control instruction to control the operation of the motor comprises controlling of a reset of the firing rod, and in response to the protrusion on the transmission member of the driving part returning back to the sensing region of the sensing part, the sensing part sends a stop signal to stop the operation of the motor to complete the reset of the firing rod.

11. The surgical stapler body according to claim 4, wherein the control unit further comprises a Hall encoder on the power unit to monitor an operation of the power unit.

12. A surgical stapler, comprising the surgical stapler body according to claim 1 and a cartridge.

13. A cartridge, comprising a storage part connected to a cartridge assembly, and information able to be stored in the storage part comprises preset stroke data of the cartridge, wherein the storage part and the cartridge assembly are detachably connected, and the storage part is an electronic tag attached to an outer circumferential surface of the cartridge assembly or an electronic tag hanged to the cartridge assembly.

14. The cartridge according to claim 13, wherein the electronic tag is a card with a magnetic stripe, an inductive electronic wafer, or an integrated circuit card.

* * * * *